United States Patent [19]

Lauk

[11] Patent Number: 5,439,486
[45] Date of Patent: * Aug. 8, 1995

[54] TRIPHENEDIOXAZINES, THEIR PREPARATION AND THE USE THEREOF

[75] Inventor: Urs Lauk, Zürich, Switzerland

[73] Assignee: Ciba-Geigy Corporation, Ardsley, N.Y.

[*] Notice: The portion of the term of this patent subsequent to Aug. 3, 2010 has been disclaimed.

[21] Appl. No.: 116,773

[22] Filed: Sep. 3, 1993

Related U.S. Application Data

[62] Division of Ser. No. 784,198, Oct. 28, 1991, Pat. No. 5,268,475.

[30] Foreign Application Priority Data

Oct. 30, 1990 [CH] Switzerland ............... 3443/90

[51] Int. Cl.⁶ ............... D06P 3/874; D06P 1/40; D06P 1/382; C09B 62/02
[52] U.S. Cl. ............... 8/532; 8/638; 8/549; 544/75; 544/76; 544/77
[58] Field of Search ............... 544/75, 76, 77; 8/532, 8/638, 549

[56] References Cited

U.S. PATENT DOCUMENTS

| | | | |
|---|---|---|---|
| 4,578,461 | 3/1986 | Jager | 544/76 |
| 4,990,615 | 2/1991 | Henk | 544/76 |
| 5,223,000 | 6/1993 | Lauk | 8/638 |

FOREIGN PATENT DOCUMENTS

| | | |
|---|---|---|
| 0124971 | 11/1984 | European Pat. Off. |
| 0256650 | 2/1986 | European Pat. Off. |
| 0299328 | 1/1989 | European Pat. Off. |
| 0356014 | 2/1990 | European Pat. Off. |
| 0361186 | 4/1990 | European Pat. Off. |
| 0425907 | 5/1991 | European Pat. Off. |
| 3832531 | 3/1990 | Germany. |
| 4005551 | 8/1990 | Germany. |
| 2228738 | 9/1990 | United Kingdom. |

*Primary Examiner*—Paul Lieberman
*Assistant Examiner*—Margaret Einsmann
*Attorney, Agent, or Firm*—Kevin T. Mansfield

[57] ABSTRACT

Dye mixtures obtainable by condensing a compound of the formula

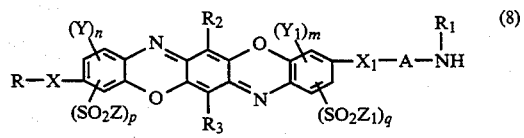

and a compound of the formula

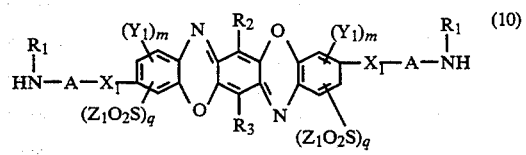

with a compound of the formula

T—B—T       (9)

where the ring substituents are as defined herein, B is a bivalent organic linking group and T is halogen are suitable for use as direct dyes for dyeing and printing a wide range of materials and especially of cellulosic fibre materials, to give dyeings and prints of good allround fastness properties.

17 Claims, No Drawings

TRIPHENEDIOXAZINES, THEIR PREPARATION AND THE USE THEREOF

This is a divisional of Ser. No. 07/784,198 filed Oct. 28, 1991 now U.S. Pat. No. 5,268,475.

The present invention relates to novel triphenedioxazines, to their preparation and to the use thereof for dyeing and printing fibre materials, especially textile fibre materials.

Specifically, the invention relates to compounds of formula

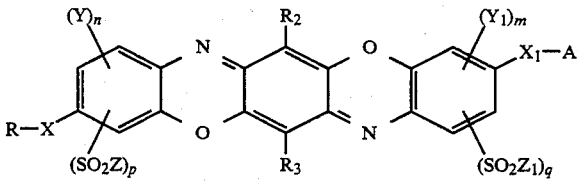

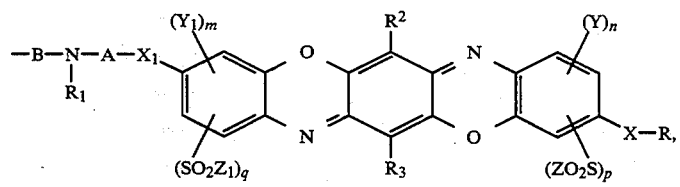

(1)

wherein R and $R_1$ are each independently of the other hydrogen or unsubstituted or substituted alkyl, cycloalkyl, aryl or aralkyl, X is a direct bond, —O—, —S— or —N($R_4$)—, wherein $R_4$ is hydrogen or unsubstituted or substituted alkyl, cycloalkyl, aryl or aralkyl, $X_1$ is —O—, —S— or —N($R_4$)—, wherein $R_4$ is hydrogen or unsubstituted or substituted alkyl, cycloalkyl, aryl or aralkyl, Y and $Y_1$ are each independently of the other $C_1$–$C_4$alkyl, $C_1$–$C_4$alkoxy, halogen, sulfo, carboxy, carbamoyl, N-mono- or N,N-di-$C_1$–$C_4$alkylcarbamoyl, N-phenyl- or N,N-diphenylcarbamoyl, sulfamoyl, N-mono- or N,N-di-$C_1$–$C_4$alkylsulfamoyl or N-phenyl- or N,N-diphenylsulfamoyl, Z and $Z_1$ are each independently of the other hydroxy or unsubstituted or substituted alkyl, aryl or aralkyl, $R_2$ and $R_3$ are each independently of the other hydrogen, halogen, cyano, $C_1$–$C_4$alkyl, $C_1$–$C_4$alkoxy, unsubstituted or substituted phenyl, benzyl, benzoylamino or phenoxy, sulfo, carboxy, carbamoyl, phenylcarbamoyl or $C_2$–$C_5$alkanoylamino, A is an unsubstituted or substituted alkylene, cycloalkylene, arylene or aralkylene radical, B is a bivalent organic linking group, and m, n, p and q are each independently of one another 0 or 1.

R and $R_1$ as an unsubstituted or substituted alkyl radical may be an unsubstituted or substituted $C_1$–$C_6$alkyl radical. Typical examples are a methyl, ethyl, n- or isopropyl or n-, iso-, sec- or tert-butyl radical or a straight-chain or branched pentyl or hexyl radical, which may be substituted by $C_1$–$C_4$alkoxy, which will be understood as meaning throughout this specification typically methoxy, ethoxy, n- or isopropoxy or n-, iso-, sec- or tert-butoxy; hydroxy; sulfo; sulfato; carboxy; cyano; halogen, which will be understood as meaning throughout this specification typically fluoro, bromo and, preferably, chloro; $C_2$–$C_5$alkoxycarbonyl, such as methoxycarbonyl or ethoxycarbonyl; $C_2$–$C_5$alkanoyloxy, such as acetoxy, propionyloxy; or carbamoyl, and/or, with the exception of methyl, which alkyl radical may be interrupted by an —O—, —S— or —NH— group.

Typical examples of suitable alkyl radicals R and $R_1$ are thus methyl, ethyl, n-propyl, isopropyl, n-, iso-, sec- or tert-butyl, β-chloroethyl, β-hydroxyethyl, β-hydroxybutyl, β-cyanoethyl, sulfomethyl, β-sulfoethyl, β-sulfatoethyl, β-acetoxyethyl, β-sulfatopropyl, γ-sulfatopropyl or the radical of formula —CH$_2$CH$_2$OCH$_2$CH$_2$OH, —CH$_2$CH$_2$NHCH$_2$CH$_2$OH or —CH$_2$CH$_2$OCH$_2$CH$_2$OSO$_3$H.

Alkyl radicals R and $R_1$ are each independently of the other preferably $C_1$–$C_4$alkyl which is unsubstituted or substituted by hydroxy, sulfo, sulfato, chloro, cyano or acetoxy, and/or with the exception of methyl, may be interrupted by a group —O—.

The particularly preferred meaning of R and $R_1$ as alkyl is an unsubstituted $C_1$–$C_4$alkyl radical and, most particularly, methyl and ethyl.

R and $R_1$ as unsubstituted or substituted cycloalkyl may be unsubstituted or substituted $C_5$–$C_9$-cycloalkyl and, preferably, cyclopentyl or cyclohexyl which is unsubstituted or substituted by $C_1$–$C_4$alkyl, typically in the context of this invention by methyl, ethyl, n- or isopropyl or n-, iso-, sec- or tert-butyl, or by amino, $C_2$–$C_5$alkanoylamino, such as acetylamino or n-propionylamino, or benzoylamino.

The particularly preferred meaning of R and $R_1$ as cycloalkyl is cyclopentyl or cyclohexyl which is unsubstituted or substituted by 1 to 3 methyl groups, and is most preferably cyclohexyl.

R and $R_1$ as aryl may be unsubstituted phenyl or naphthyl or phenyl or naphthyl which may be substituted by sulfo, nitro, halogen, cyano, $C_1$–$C_4$alkyl, $C_1$–$C_4$alkoxy, hydroxy, phenoxy, amino, N-mono-or N,N-di-$C_1$–$C_4$alkylamino, $C_2$–$C_5$alkanoylamino, benzoylamino, $C_1$–$C_4$alkoxycarbonyl, carbamoyl, sulfamoyl, carboxy and/or $C_1$–$C_4$alkylsulfonyl.

R and $R_1$ as aryl are each independently of the other preferably unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl, or are unsubstituted 1- or 2-naphthyl or 1- or 2-naphthyl which is substituted by sulfo, nitro and/or chloro.

The particularly preferred meaning of R and $R_1$, each independently of the other, as aryl is an unsubstituted phenyl radical or a phenyl radical which is substituted by sulfo, chloro, methyl and/or methoxy.

An aralkyl radical R and $R_1$ may be unsubstituted or substituted $C_7$–$C_{12}$aralkyl and, preferably, benzylethyl or phenylethyl which may be further substituted by $C_1$–$C_4$alkyl, sulfo, nitro, halogen or $C_1$–$C_4$alkoxy. The particularly preferred meaning of R and $R_1$, each independently of the other, as aralkyl is unsubstituted benzyl, or benzyl which is substituted by methyl, sulfo, chloro and/or methoxy, and is most preferably benzyl.

R and $R_1$ are each independently of the other preferably hydrogen, unsubstituted $C_1$–$C_4$alkyl or $C_1$–$C_4$alkyl which is substituted by hydroxy, sulfo, sulfato, chloro, cyano, or acetoxy and/or, with the exception of methyl, may be interrupted by a group —O—; cyclopentyl or cyclohexyl which are unsubstituted or substituted by 1 to 3 methyl groups; unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl; unsubstituted 1- or 2-naphthyl or 1- or 2-naphthyl which is substituted by sulfo, nitro and/or chloro; or unsubstituted benzyl or benzyl which is substituted by methyl, methoxy, sulfo and/or chloro.

More particularly, R and $R_1$ are each independently of the other hydrogen, $C_1$–$C_4$alkyl, cyclohexyl, unsubstituted phenyl or benzyl or phenyl or benzyl which are substituted by sulfo, chloro, methyl and/or methoxy, and are most preferably hydrogen, methyl or ethyl. In a particularly preferred embodiment of the invention R and $R_1$ are each hydrogen.

An unsubstituted or substituted alkylene radical A may be an unsubstituted or substituted $C_2$–$C_6$alkylene radical and, preferably, a $C_2$–$C_6$alkylene radical which is unsubstituted or substituted by hydroxy, sulfo, sulfato, $C_1$–$C_4$alkoxy, carboxy, cyano, halogen, phenyl, sulfophenyl or $C_2$–$C_5$alkoxycarbonyl, and/or which may be interrupted by 1 or 2 —O— or —N($R_5$)— groups, wherein $R_5$ is $C_1$–$C_4$alkyl, acetyl or, preferably, hydrogen, or by —S—, —$SO_2$— or a cycloaliphatic or heterocyclic-aliphatic radical.

Exemplary of suitable radicals A are 1,2-ethylene, 1,2- and 1,3-propylene, 1-ethyl-1,2-ethylene, 2-hydroxy-1,3-propylene, 2-sulfato-1,3-propylene, 1- and 2-phenyl-1,3-propylene, 2-(4′-sulfophenyl)-1,3-propylene, 1,4-, 2,3- and 2,4-butylene, 1,2-dimethyl-1,2-ethylene, 1-phenyl-1,2-ethylene, 2-methyl-1,3-propylene, 2,2-dimethyl-1,3-propylene, 1-chloro-2,3-propylene, 1,5- and 2,4-pentylene, 2-methyl-2,4-pentylene, 1-carboxy-1,5-pentylene, 2,3-diphenyl-1,4-butylene, 1-methoxycarbonyl-1,5-pentylene, 1,6 and 2,5-hexylene, 2-carboxy-1,3-propylene, 2-methoxy-1,3-propylene, a radical of formula —$CH_2$—$CH_2$—Z′—$CH_2$—$CH_2$—, wherein Z′ is —O—, —S—, —$SO_2$—, —NH— or —N($CH_3$)— or a radical of formula

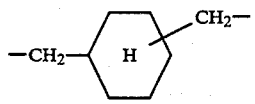

or

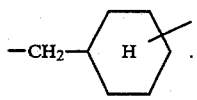

or

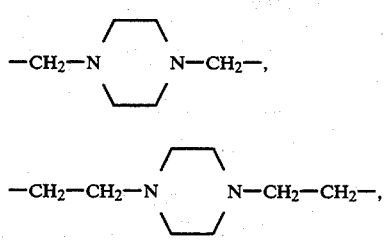

A as alkylene is more particularly a $C_2$–$C_4$alkylene radical which is unsubstituted or substituted by hydroxy, sulfo, sulfato, methoxy, carboxy or sulfophenyl, and, most preferably, a 1,2-ethylene or 1,2- or 1,3-propylene radical which is unsubstituted or substituted by hydroxy or sulfato. In a particularly preferred embodiment of the invention, A is 1,2-ethylene, 1,2- or 1,3-propylene or 2-sulfato-1,3-propylene.

A as unsubstituted or substituted cycloalkylene may be unsubstituted or substituted $C_5$–$C_9$cycloalkylene and preferably cyclopentylene or cyclohexylene which are unsubstituted or substituted by one or more $C_1$–$C_3$alkyl groups. Most preferably A is unsubstituted cyclohexylene or cyclohexylene which is substituted by 1 to 3 methyl groups.

Typical examples of suitable cycloaliphatic radicals A are: 1,3- and 1,4-cyclohexylene, 4-methyl-1,3-cyclohexylene, 2-methyl-1,3-cyclohexylene, 5,5-dimethyl-1,3-cyclohexylene, 2-methyl-1,4-cyclohexylene, 4,6-dimethyl-1,3-cyclohexylene and 4-methyl-1,2-cyclohexylene.

A as a bivalent aryl radical may be a phenylene, biphenylene or naphthylene radical which is unsubstituted or substituted by $C_1$–$C_4$alkyl, $C_1$–$C_4$alkoxy, sulfo, halogen or carboxy.

Exemplary of arylene radicals A are: 1,3- and 1,4-phenylene, 2-sulfo-1,4-phenylene, 2,5-disulfo-1,4-phenylene, 4-sulfo-1,3-phenylene, 2-methyl-1,4-phenylene, 2-carboxy-1,4-phenylene, 2-methoxy-1,4-phenylene, 4,8-disulfo-2,6-naphthylene, 8-sulfo-2,6-naphthylene, 1,4-naphthylene and 1,1′-biphenyl-4,4′-diyl.

An arylene radical A is preferably a 1,3- or 1,4-phenylene radical which is unsubstituted or substituted by sulfo, methyl, methoxy or carboxy, or an unsubstituted or sulfo-substituted naphthylene radical.

Most preferably, an arylene radical A is unsubstituted or sulfo-substituted 1,3- or 1,4-phenylene.

An unsubstituted or substituted aralkylene radical A may be a $C_1$–$C_6$alkylene-phenylene, phenylene-$C_1$–$C_6$alkylene-phenylene, $C_1$–$C_3$alkylene-phenylene-$C_1$–$C_3$alkylene or methylene-naphthylene-methylene radical, in which aralkylene radicals the alkylene moiety may be substituted as previously indicated and/or interrupted by one of the aforementioned hetero groups, and the phenylene and naphthylene moiety may additionally carry 1 or 2 substituents selected from the group consisting of sulfo, carboxy, sulfamoyl, carbamoyl, methyl, ethyl, methoxy, ethoxy, nitro, chloro, amino, N-methylamino and N-ethylamino, N,N-dimethylamino and N,N-diethylamino and phenylamino.

Exemplary of suitable aralkylene radicals A are:

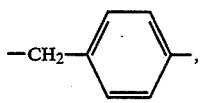

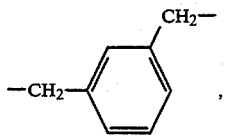

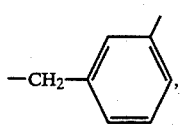

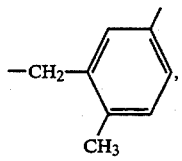

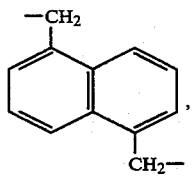

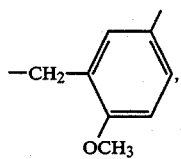

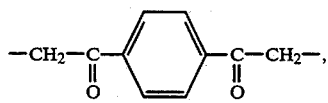

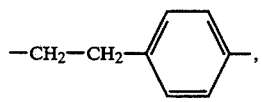

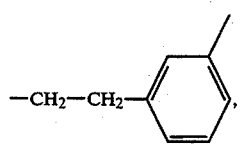

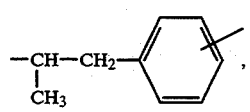

-continued

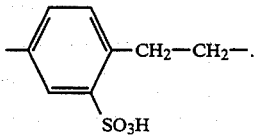

An aralkylene radical A is preferably $C_1$-$C_3$alkylene-phenylene or $C_1$-$C_2$alkylenephenylene-$C_1$-$C_2$alkylene which are unsubstituted or substituted in the phenyl moiety by methyl, methoxy, chloro or sulfo.

A is preferably a $C_2$-$C_4$alkylene radical which is unsubstituted or substituted by hydroxy, sulfo, sulfato, methoxy, carboxy, or sulfophenyl, —$CH_2$—$CH_2$—$Z'$—$CH_2$—$CH_2$—, wherein $Z'$ is —O—, —S—, —$SO_2$—, —NH— or —N($CH_3$)—, a cyclohexylene radical which is unsubstituted or substituted by 1 to 3 methyl groups, an unsubstituted or sulfo-substituted 1,3- or 1,4-phenylene radical, or a $C_1$-$C_3$alkylene-phenylene or $C_1$-$C_2$alkylene-phenylene-$C_1$-$C_2$alkylene radical, wherein the phenylene moiety is unsubstituted or substituted by methyl, methoxy, chloro or sulfo.

$R_4$ as unsubstituted or substituted alkyl, cycloalkyl, aryl or aralkyl has the meanings and preferred meanings given previously for R.

$R_4$ is preferably hydrogen, $C_1$-$C_4$alkyl, cyclohexyl, unsubstituted phenyl or benzyl or phenyl or benzyl which are substituted by sulfo, chloro, methyl and/or methoxy.

Particularly preferred meanings of $R_4$ are hydrogen and $C_1$-$C_4$alkyl, more particularly hydrogen, methyl and ethyl and, most preferably, hydrogen.

X and $X_1$ are each independently of the other preferably a group —N($R_4$)—, wherein $R_4$ has the meanings and preferred meanings given hereinbefore. Most preferably, X and $X_1$ are each a —NH— group.

Y and $Y_1$ are each independently of the other preferably sulfo, $C_1$-$C_4$alkyl, $C_1$-$C_4$alkoxy or chloro and, most preferably, methoxy, methyl, chloro or sulfo. Y and $Y_1$ may have a different or preferably the identical meaning.

The variables n and m are preferably 0.

Aryl or aralkyl radicals Z and $Z_1$ have independently of each other the meanings and preferred meanings previously given for $R_1$.

An unsubstituted or substituted alkyl radical Z and $Z_1$ may be an unsubstituted or substituted $C_1$-$C_6$alkyl radical, typically a $C_1$-$C_6$alkyl radical which is unsubstituted or substituted by hydroxy, $C_1$-$C_4$alkoxy or carboxy, and which, with the exception of methyl, may be interrupted by —O—, —S— or —N($R_5$)—, wherein $R_5$ is as previously defined.

Z and $Z_1$ as alkyl are each independently of the other preferably is unsubstituted $C_1$-$C_4$alkyl and, more particularly, methyl or ethyl.

Z and $Z_1$ are preferably each methyl or ethyl and, most preferably, are each hydroxy.

p and q are preferably 1.

Where $R_2$ and/or $R_3$ are defined as unsubstituted or substituted phenyl, benzyl, benzoylamino or phenoxy, the phenyl ring may be unsubstituted or substituted by $C_1$-$C_4$alkyl, $C_1$-$C_4$alkoxy, acetylamino, halogen, nitro and/or sulfo. Preferably the phenyl ring carries no further substituents or is substituted by chloro, methyl, methoxy, acetylamino and/or sulfo.

The radicals $R_2$ and $R_3$ may be different or, preferably, identical.

$R_2$ and $R_3$ are preferably, however, hydrogen, fluoro, chloro, bromo, methyl, methoxy, acetylamino, phenoxy or cyano and, most preferably, bromo or chloro.

A preferred embodiment of the invention relates to compounds of formula (1), wherein $R_2$ and $R_3$ are each chloro.

The bivalent organic linking group B may be a radical of formula

  (2), wherein E for example is a direct bond, an unsubstituted or substituted alkylene, alkenylene, cycloalkylene, alkylene-cyclohexylene, arylene, aralkylene, heterocyclylene, biphenyl or stilbene radical, Q is a group

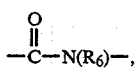

or

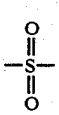

and $R_6$ is unsubstituted or substituted alkyl, aryl, cycloalkyl or aralkyl, or is preferably hydrogen.

Where E is defined as unsubstituted or substituted cycloalkylene, arylene or aralkylene, the meanings and preferred meanings previously given for A apply independently of one another. The alkylene-cyclohexylene, biphenyl or stilbene radicals can be substituted as indicated for A defined as cyclohexylene or arylene.

E defined as alkylene may have one of the meanings previously given for A defined as unsubstituted or substituted alkylene or may be methylene. E defined as alkylene is preferably $C_1$–$C_4$alkylene which is unsubstituted or substituted by hydroxy, sulfo, sulfato, methoxy, carboxy, phenyl or sulfophenyl, and is most preferably methylene, 1,2-ethylene or 1,2- or 1,3-propylene.

A heterocyclyl radical E may be the piperazine-1,4-diyl, furan-2,5-diyl or thiophene-2,5-diyl radical.

$R_6$ as unsubstituted or substituted alkyl, cycloalkyl, aryl or aralkyl has the meanings and preferred meanings previously given for R.

Preferred organic linking groups B are the radicals of formula (2), wherein Q is a group

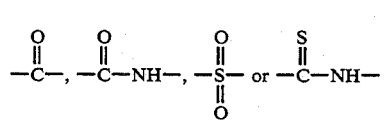

E is a direct bond, $C_1$–$C_6$alkylene or $C_2$–$C_6$alkenylene, each unsubstituted or substituted by hydroxy, sulfo, sulfato, methoxy, carboxy, phenyl or sulfophenyl, or is cyclohexylene or $C_1$–$C_2$alkylene-cyclohexylene, each unsubstituted or substituted by 1 to 3 methyl groups, or is piperazine-1,4-diyl, thiophene-2,5-diyl, biphenyl-4,4'-diyl, stilbene-4,4'-diyl, unsubstituted phenylene or naphthylene, or phenylene or naphthylene which are each substituted by $C_1$–$C_4$alkyl, $C_1$–$C_4$alkoxy, sulfo, halogen or carboxy, or $C_1$–$C_3$alkylene-phenylene or $C_1$–$C_2$alkylene-phenylene-$C_1$–$C_2$alkylene, each unsubstituted or substituted in the phenyl moiety by methyl, methoxy, chloro or sulfo.

Especially preferred bivalent linking groups B have the formula

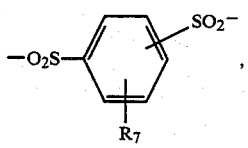

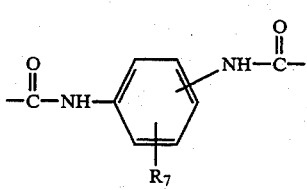

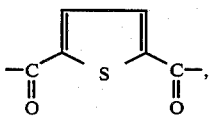

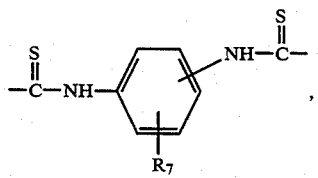

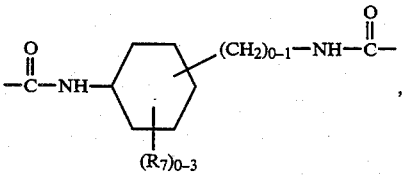

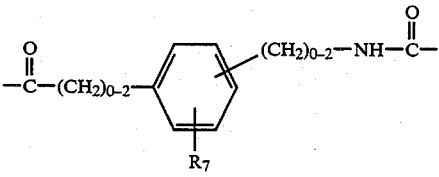

-continued

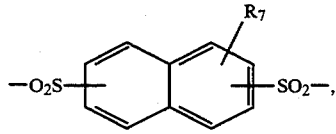

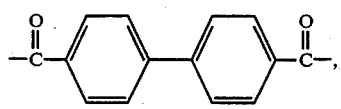

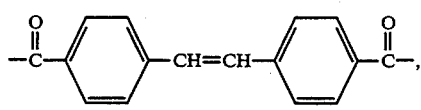

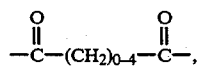

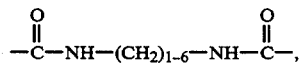

or

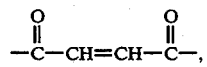

wherein $R_7$ is sulfo, methyl, methoxy, chloro, carboxy or, preferably, hydrogen.

A particularly preferred embodiment of the invention relates to compounds of formula (1), wherein B is a radical of formula

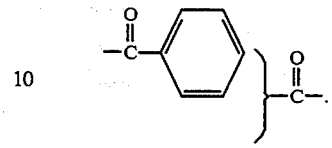

A further group of suitable linking groups B comprises those groups which contain or consist of at least one nitrogen-containing aromatic-heterocyclic radical. Exemplary of such aromatic-heterocyclic linking groups B are a radical of formula

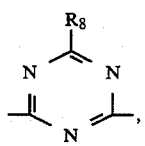  (3)

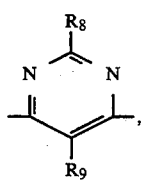  (4)

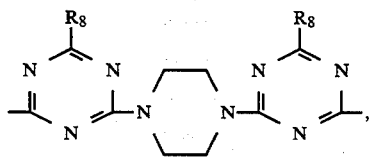  (5)

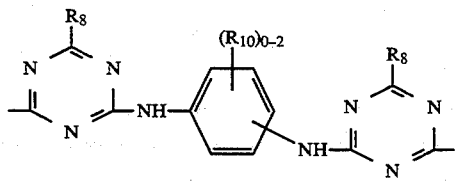  (6)

or

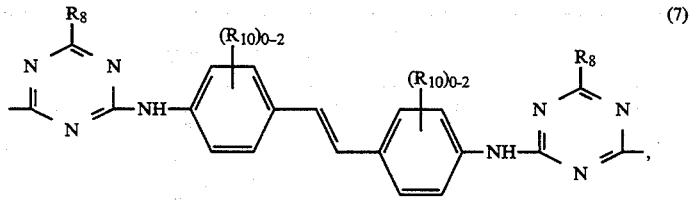  (7)

wherein $R_9$ is nitro, cyano, $C_1$-$C_4$alkylsulfonyl, carboxy, chloro, fluoro, $C_1$-$C_4$alkoxysulfonyl, $C_1$-$C_4$alkylsulfinyl, $C_1$-$C_4$alkoxycarbonyl or $C_1$-$C_4$alkanoyl and, preferably, cyano, chloro, fluoro, methylsulfonyl, ethylsulfonyl or formyl, $R_{10}$ is sulfo, $C_1$-$C_4$alkyl, $C_1$-$C_4$alkoxy or halogen, preferably sulfo, methyl or methoxy and, most preferably, sulfo, and $R_8$ is a substituent which is not fibre-reactive.

Exemplary of suitable substituents $R_8$ which are not fibre-reactive are chloro, hydroxy, $C_1$-$C_4$alkyl, phenyl, $C_1$-$C_4$alkoxy, $C_1$-$C_4$alkylthio, amino, N-mono- or N,N- di-$C_1$–$C_4$alkylamino which is unsubstituted or substituted in the alkyl moiety by hydroxy, carboxy, cyano, sulfo, sulfato or $C_1$–$C_4$alkoxy; cyclohexylamino; phenylamino or N-$C_1$–$C_4$alkyl-N-phenylamino which are unsubstituted or substituted in the phenyl moiety by $C_1$–$C_4$alkyl, $C_1$–$C_4$alkoxy, phenoxy, carboxy, sulfo and/or halogen; morpholino or 3-carboxy- or 3-carbamoylpyridin-1-yl.

$R_8$ in each of formulae (3), (4), (5), (6) and (7) is preferably chloro, hydroxy, $C_1$–$C_4$alkoxy, $C_1$–$C_2$alkylthio, amino, N-mono- or N,N-di-$C_1$–$C_4$alkylamino which is unsubstituted or substituted in the alkyl moiety by hydroxy, sulfo or sulfato; cyclohexylamino; phenylamino or N-$C_1$–$C_4$alkyl-N-phenylamino which is unsubstituted or substituted in the phenyl moiety by methyl, methoxy, carboxy, sulfo or chloro, or is morpholino.

Illustrative examples of especially preferred radicals $R_8$ are hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m- or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino and morpholino.

A further preferred group of useful linking groups B comprises those of formulae

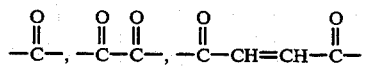

and

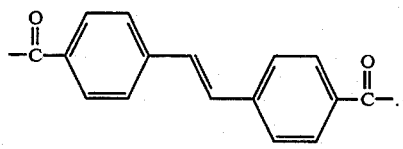

Preferred linking groups B have the formula

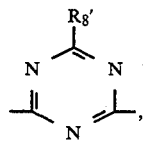  (2')

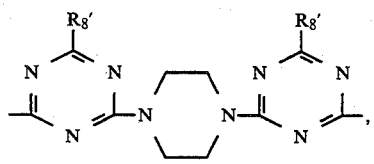  (3')

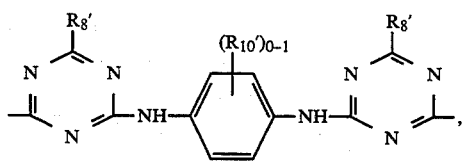  (5')

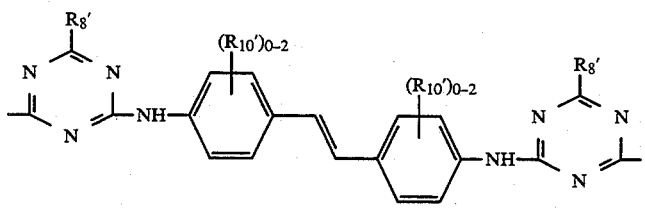  (6')

or

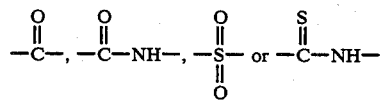  (7')

wherein Q' is a group $$-\overset{O}{\underset{\|}{C}}-,\quad -\overset{O}{\underset{\|}{C}}-NH-,\quad -\overset{O}{\underset{\underset{\|}{O}}{\overset{\|}{S}}}-\quad \text{or} \quad -\overset{S}{\underset{\|}{C}}-NH-$$

E' is a direct bond, $C_1$–$C_6$alkylene or $C_2$–$C_6$alkenylene which are unsubstituted or substituted by hydroxy, sulfo, sulfato, methoxy, carboxy, phenyl or sulfophenyl, cyclohexylene or $C_1$–$C_2$alkylene-cyclohexylene which are unsubstituted or substituted by 1 to 3 methyl groups, or is piperazine-1,4-diyl, thiophene-2,5-diyl, biphenyl-4,4'-diyl, stilbene-4,4'-diyl, unsubstituted phenylene or naphthylene, or phenylene or naphthylene which are substituted by $C_1$–$C_4$alkyl, $C_1$–$C_4$alkoxy, sulfo, halogen or carboxy, or is $C_1$–$C_3$alkylene-phenylene or $C_1$–$C_2$alkylene-phenylene-$C_1$–$C_2$alkylene which are unsubstituted or substituted in the phenyl moiety by methyl, methoxy, chloro or sulfo, R'$_8$ is chloro, hydroxy, $C_1$–$C_4$alkoxy, $C_1$–$C_2$alkylthio, amino, N-mono- or N,N-di-$C_1$–$C_4$alkylamino which are unsubstituted or substituted in the alkyl moiety by hydroxy, sulfo or sulfato, or is cyclohexylamino, phenylamino or N-$C_1$–$C_4$alkyl-N-phenylamino which are unsubstituted or substituted in the phenyl moiety by methyl, methoxy, carboxy, sulfo or chloro, or is morpholino, and $R'_{10}$ is sulfo, methyl or methoxy.

Particularly preferred bivalent linking groups B are the radicals of formula

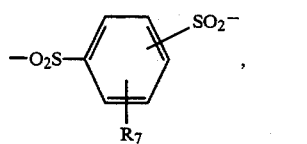

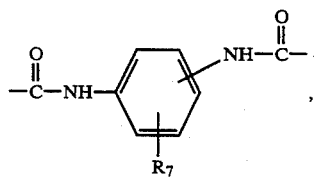

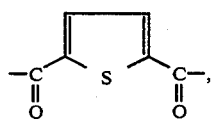

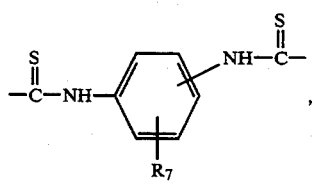

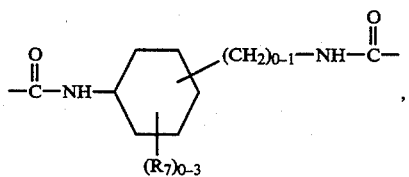

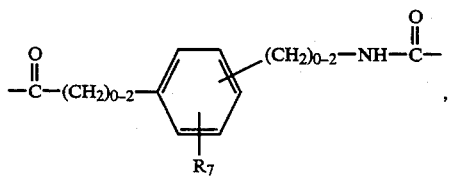

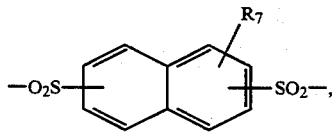

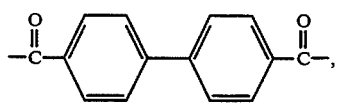

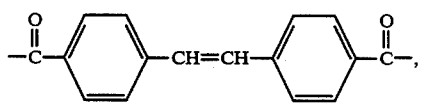

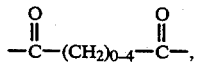

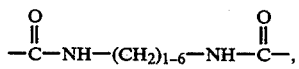

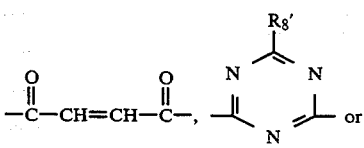

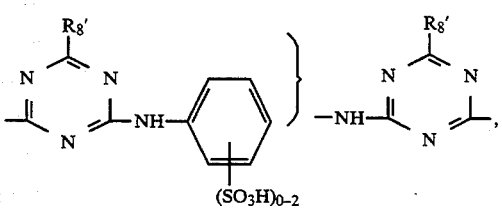

wherein $R_7$ is sulfo, methyl, methoxy, chloro, carboxy, or preferably, hydrogen, and $R'_8$ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

Because of their good tinctorial properties, important of compounds of formula (1) as indicated above are those wherein R and $R_1$ are each independently of the other hydrogen, unsubstituted $C_1$–$C_4$alkyl or $C_1$–$C_4$alkyl which is substituted by hydroxy, sulfo, sulfato, chloro, cyano, or acetoxy and/or, with the exception of methyl, may be interrupted by a group —O—, unsubstituted cyclopentyl or cyclohexyl, or cyclopentyl or cyclohexyl which are substituted by 1 to 3 methyl groups, unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl, or is unsubstituted 1- or 2-naphthyl or 1- or 2-naphthyl which is substituted by sulfo, nitro and/or chloro, or is unsubstituted benzyl or benzyl which is substituted by methyl, methoxy, sulfo and/or chloro, A is a $C_2$–$C_4$alkylene radical which is unsubstituted or substituted by hydroxy, sulfo, sulfato, methoxy, carboxy or sulfophenyl, or is —CH$_2$—CH$_2$—Z'—CH$_2$—CH$_2$—, wherein Z' is —O—, —S—, —SO$_2$—, —NH— or —N(CH$_3$)—, a cyclohexylene radical which is unsubstituted or substituted by 1 to 3 methyl groups, an unsubstituted or sulfo-substituted 1,3- or 1,4-phenylene radical or is a $C_1$–$C_3$alkylene-phenylene or $C_1$–$C_2$alkylene-phenylene-$C_1$–$C_2$alkylene radical, wherein the phenylene moiety is unsubstituted or substituted by methyl, methoxy, chloro or sulfo, X and $X_1$ are each independently of the other a group —N(R$_4$)—, wherein R$_4$ is hydrogen, $C_1$–$C_4$alkyl, cyclohexyl, unsubstituted phenyl or benzyl or phenyl or benzyl which are substituted by sulfo, chloro, methyl and/or methoxy, Y and $Y_1$ are each independently of the other methoxy, methyl, chloro or sulfo, n and m are each independently of the other 0 or 1, Z and $Z_1$ are each independently of the other hydroxy, methyl or ethyl, p and q are each 1, $R_2$ and $R_3$ are each hydrogen, fluoro, chloro, bromo, methyl, methoxy, acetylamino, phenoxy or cyano, and the linking group B has the formula

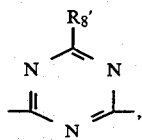 (2')

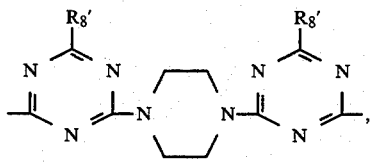 (3')

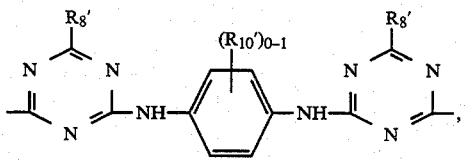 (5')

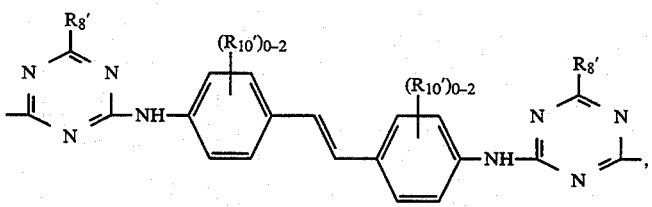 (6')

or

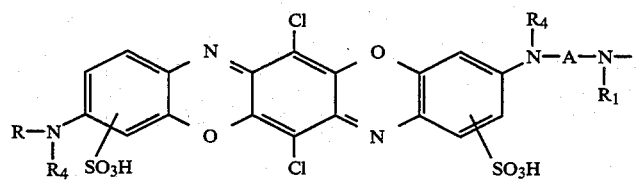 (7')

wherein Q' is a group

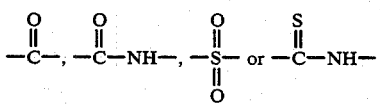

E' is a direct bond, $C_1-C_6$alkylene or $C_2-C_6$alkenylene which are unsubstituted or substituted by hydroxy, sulfo, sulfato, methoxy, carboxy, phenyl or sulfophenyl, or is cyclohexylene or $C_1-C_2$alkylene-cyclohexylene which are unsubstituted or substituted by 1 to 3 methyl groups; piperazine-1,4-diyl, thiophene-2,5-diyl, biphenyl-4,4'-diyl, stilbene-4,4'-diyl; unsubstituted phenylene or naphthylene, or phenylene or naphthylene which are substituted by $C_1-C_4$alkyl, $C_1-C_4$alkoxy, sulfo, halogen or carboxy; or $C_1-C_3$alkylene-phenylene or $C_1-C_2$alkylene-phenylene-$C_1-C_2$alkylene which are unsubstituted or substituted in the phenyl moiety by methyl, methoxy, chloro or sulfo, $R'_8$ is chloro, hydroxy, $C_1-C_4$alkoxy, $C_1-C_2$alkylthio, amino, N-mono- or N,N-di-$C_1-C_4$alkylamino which are unsubstituted or substituted in the alkyl moiety or moieties by hydroxy, sulfo or sulfato, cyclohexylamino, phenylamino or N-$C_1-C_4$alkyl-N-phenylamino which are unsubstituted or substituted in the phenyl moiety by methyl, methoxy, carboxy, sulfo or chloro, or morpholino, and $R'_{10}$ is sulfo, methyl or methoxy.

Of particular importance on account of their good tinctorial properties are compounds of formula

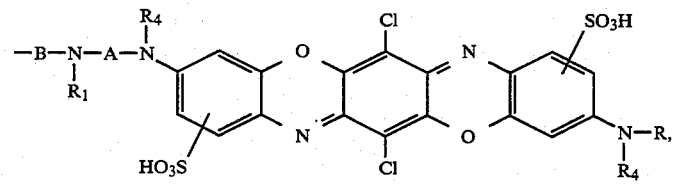 (1a)

wherein R and $R_1$ are each independently of the other hydrogen, $C_1-C_4$alkyl, cyclohexyl, unsubstituted phenyl or benzyl, or phenyl or benzyl which are substituted by sulfo, chloro, methyl and/or methoxy, A is a $C_2-C_4$alkylene radical which is unsubstituted or substituted by hydroxy, sulfo, sulfato, methoxy, carboxy or sulfophenyl, R₄ is hydrogen, methyl or ethyl, and B is a radical of formula

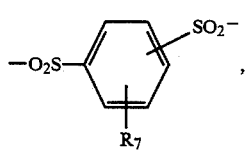

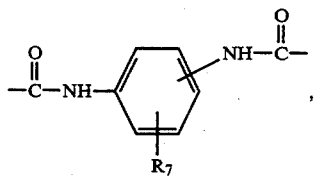

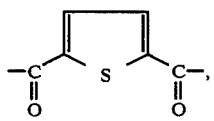

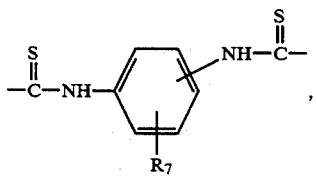

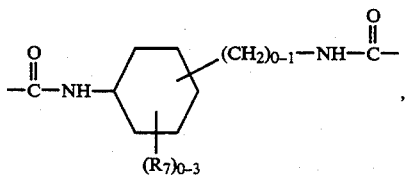

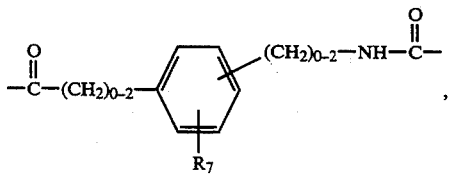

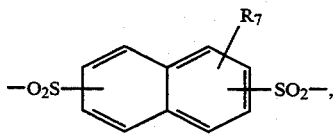

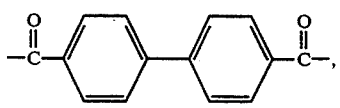

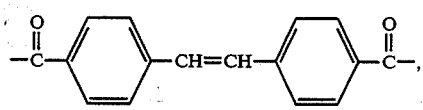

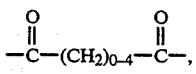

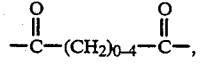

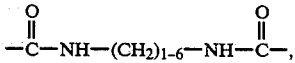

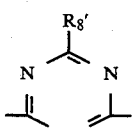

or

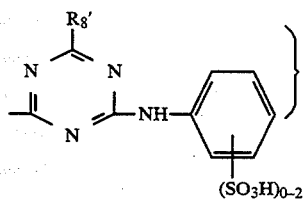

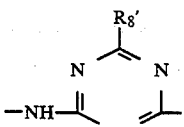

wherein $R_7$ is sulfo, methyl, methoxy, chloro, carboxy or, preferably, hydrogen, and $R'_8$ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

A particularly preferred embodiment of the invention relates to compounds of formula

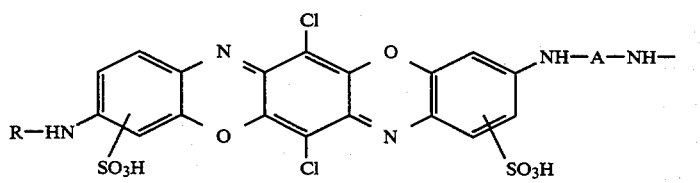

(1b)

-continued

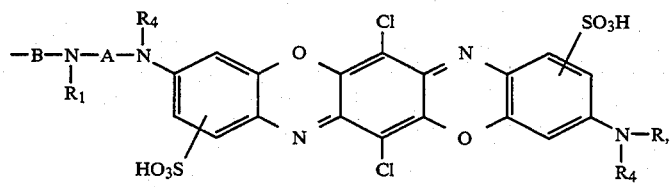

wherein R is methyl, ethyl, benzyl, or, preferably, hydrogen, A is a 1,2-ethylene or 1,2- or 1,3-propylene radical which is unsubstituted or substituted by hydroxy or sulfato, and B is a radical of formula

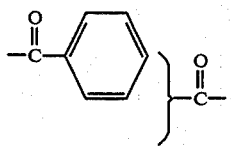

or

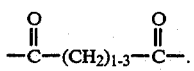

The compounds of formula (1) may be obtained by condensing a compound of formula

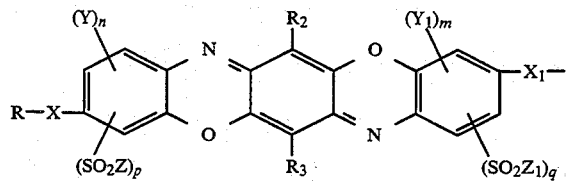

with a compound of formula

 (9)

wherein A, B, R, $R_1$, $R_2$, $R_3$, X, $X_1$, Y, $Y_1$, Z, $Z_1$, m, n, p and q are each as defined hereinbefore, and T is halogen, preferably chloro.

The condensation reaction is conveniently carried out in an aqueous or aqueous-organic medium in the temperature range from 0° to 100° C., preferably from 0° to 50° C. The reaction is conveniently carded out in the neutral to alkaline pH range, i.e. typically at pH 7-13, preferably 8-12. The pH can be adjusted by addition of bases, such as hydroxides or carbonates of alkali metals, ammonia or organic amines, and kept constant during the condensation reaction.

The compounds of formulae (8) and (9) are typically used in a molar ratio of 1.5:1 to 2:1, preferably 1.7:1 to 2:1.

The compounds of formula (8) are disclosed in EP-A 0 356 014 or they can be prepared by the methods described therein. The compounds of formula (9) are known or they can be obtained in a manner known per se.

The invention further relates to dye mixtures which are obtainable by condensing a compound of formula (8) as indicated above and a compound of formula

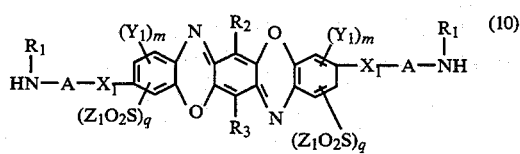

wherein A, $R_1$, $R_2$, $R_3$, $X_1$, $Y_1$, $Z_1$, m and q are each as defined for formula (1), with a compound of formula (9) as indicated above. The reaction normally proceeds as described above for the reaction of the compounds of formulae (8) and (9), but using in place of the compound of formula (8) an equimolar amount of a mixture comprising one compound of formula (8) and one compound of formula (10). It has been found useful to use the compounds of formulae (8) and (10) in the process in the weight ratio of typically 95:5 to 50:50, preferably 90:10 to 60:40 and, most preferably, 80:20 to 65:35.

The compounds of formula (10) are known or they can be obtained in a manner known per se.

The compounds of formulae (8) and (10) can be prepared independently of each other and used in the process.

Mixtures of compounds of formulae (8) and (10) can, however, also be synthesised direct, for example by reacting a compound of formula

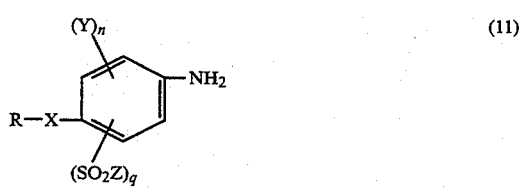

and a compound of formula

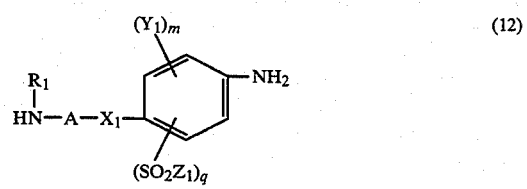

in a manner which is known per se and commonly used for the synthesis of triphenedioxazines with a 1,4-benzoquinone of formula

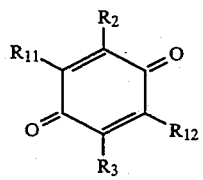
(13)

wherein R, R$_1$, R$_2$, R$_3$, A, X, X$_1$, Y, Y$_1$, Z, Z$_1$, m, n, p and q are each as defined for formula (1) and R$_{11}$ and R$_{12}$ have each independently of the other one of the meanings given for R$_2$.

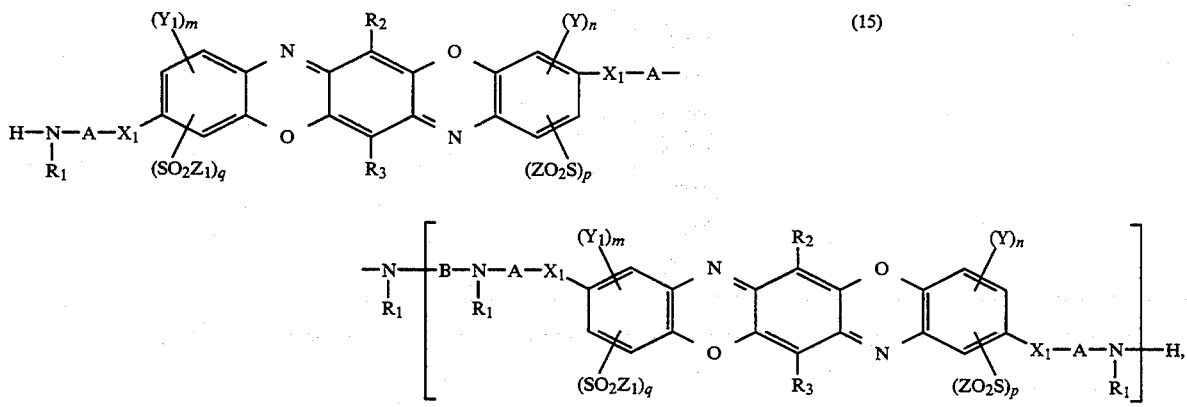

The reaction of the compounds of formulae (11), (12) and (13) with one another results in a mixture of compounds which, in addition to a compound of formula (8) and a compound of formula (10), contains as further component a compound of formula

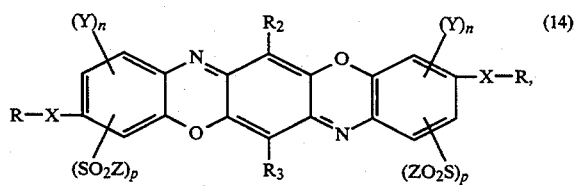
(14)

wherein R, R$_2$, R$_3$, X, Y, Z, n and p are each as defined for formula (1). However, this does not adversely affect the use of the inventive mixture for the further reaction with a compound of formula (9) or the tinctorial properties of the resultant dye mixture.

The dye mixtures obtainable by reacting a compound of each of formulae (8), (9) and (10) contain, as main components, a) a compound of formula (1) as indicated above,
b) oligomers of the probable formula (15)

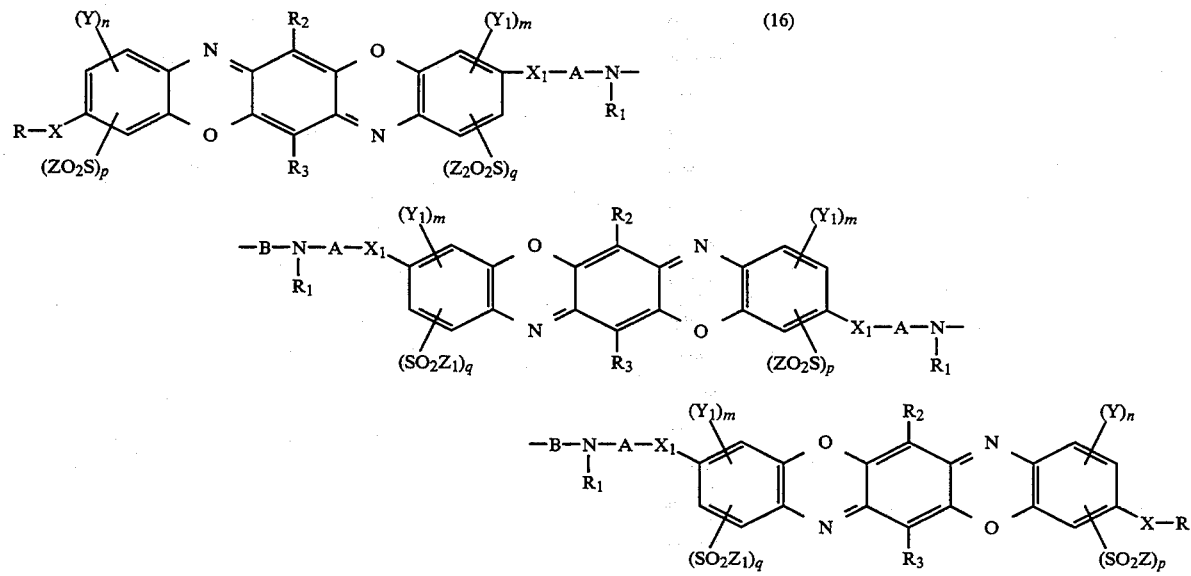

wherein A, B, R$_1$, R$_2$, R$_3$, X$_1$, Y$_1$, Z$_1$, m and q are each as defined for formula (1), and t is 1, 2, 3, 4, 5 or 6, and c) a compound of the probable formula (16)

wherein A, B, R, R$_1$, R$_2$, R$_3$, X, X$_1$, Y, Y$_1$, Z, Z$_1$, m, n, p and q are each as defined for formula (1).

The invention further relates to the use of the compounds of formula (1) and of the mixtures of compounds obtainable by reacting a compound of each of formulae (8), (9) and (10) as dyes for dyeing or printing nitrogen-containing and, preferably, hydroxyl group-containing fibre materials.

The novel compounds of formula (1) are thus suitable for dyeing and printing nitrogen-containing or, more particularly, cellulosic fibre materials, preferably textile fibre materials, made of silk, wool or synthetic polyamides, as well as preferably of cellulosic fibres such as rayon, cotton or hemp. With respect to their tinctorial properties, they may be termed as direct dyes (C.I. direct dyes).

It is also possible to dye textile fibre materials made from blends, such as wool/cotton, polyamide/cotton, acrylic/cotton or, preferably, polyester/cotton blends, by single bath processes and in the presence of dyes for the respective different type of fibre.

The textile fibre materials may be in any form of presentation, such as fibres, yarn, woven or knitted fabrics. Besides the textile substrates, leather and paper can also be dyed with the dye mixtures of this invention.

Level dyeings in blue shades of good allround fastness properties, especially good fastness to rubbing, wet treatments, wet rubbing, perspiration and light, are obtained. Where necessary, the wetfastness properties, especially washfastness, of the direct dyeings and prints can be substantially enhanced by an aftertreatment with fixing agents.

The novel dyes and dye mixtures have good compatibility with other dyes, especially disperse dyes. The novel dyes and dye mixtures have a sufficient high temperature stability and can hence be used for dyeing under the dyeing conditions for polyester fibres, i.e. in the temperature range from c. 100° to 150° C., preferably from 100° to 130° C., from an aqueous liquor and in the pH range from 4 to 7.5, preferably from 5 to 7.

It is thereby possible to use customary disperse dyes together with the dyes and dye mixtures of this invention in a single step, one bath process for dyeing polyester/cotton blends, in which process level and fast dyeings are obtained with the respective dye on both types of fibre. By using a disperse dye of the same shade as the novel dye mixture it is also possible to obtain solid shade dyeings.

The dyeing of textile blends, such as blends of polyester and cellulosic fibres, can be greatly simplified by using the dyes and dye mixtures of this invention. The conventional practice of dyeing each component of a fibre blend in a separate procedure under different dyeing conditions is therefore no longer necessary.

The novel compounds of formula (1) and mixtures of compounds are also suitable for the preparation of aqueous inks for ink-jet printing.

The following Examples will serve to illustrate the invention. Unless otherwise indicated, parts and percentages are by weight. The relationship between parts by weight and parts by volume is the same as that between the kilogram and the litre.

EXAMPLE 1

118 parts of the compound of formula

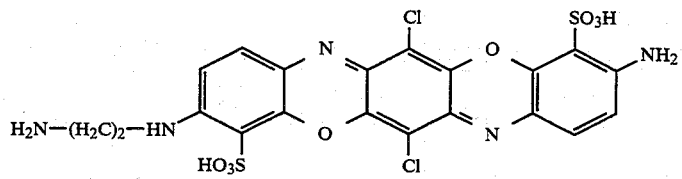

(preparation according to EP 0 356 014, Example 68) are suspended in 3000 parts of water and the pH of the suspension is adjusted with sodium hydroxide solution to about 11–12. Over about 30 minutes, 22.5 parts of terephthaloyl dichloride in 200 parts of tetrahydrofuran are added dropwise at 0°–5°, while keeping the pH at 11–12 with sodium hydroxide solution. The reaction mixture is then kept for about 2 hours at room temperature and pH 11–12, while adding further sodium hydroxide solution. The pH is then adjusted to about neutral with hydrochloric acid and the product is salted out. The batch is stirred for a further 30 minutes and the product is then isolated by filtration. The product conforms to formula (1), wherein R and $R_1$ are each hydrogen, X and $X_1$ are each —NH—, Z and $Z_1$ are each hydroxy, n and m are each 0, p and q are each 1, $R_2$ and $R_3$ are each chloro, A is 1,2-ethylene and B is a radical of formula

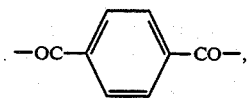

and it dyes cotton in a blue shade of good allround fastness properties.

EXAMPLE 1a

The procedure of Example 1 is repeated, replacing terephthaloyl dichloride with the equivalent amount of isophthaloyl dichloride, to give a comparable dye which dyes cotton in a blue shade of good allround fastness properties.

EXAMPLE 2 a) 17.9 parts of 1,4-diaminobenzene-2-sulfonic acid (52.5%) and 38.1 parts of 4-(3-aminopropylamino)aniline-3-sulfonic acid (96.5%) are suspended in 1500 parts of water and 300 parts of isopropanol. The suspension is adjusted by addition of phosphate buffer mixture and sodium hydroxide solution to pH 5.5–6.0 and heated, with stirring, to 50°. To the warm suspension are added 49.2 parts of chloranil, while keeping the pH at 6 by addition of potassium hydrogencarbonate solution. The reaction mixture is allowed to continue to react for about a further 4 hours, cooled to room temperature, and the precipitated solid is isolated by filtration, washed copiously with water and then with acetone.

The product is a mixture consisting of 1.2–1.4 parts of the compound of formula

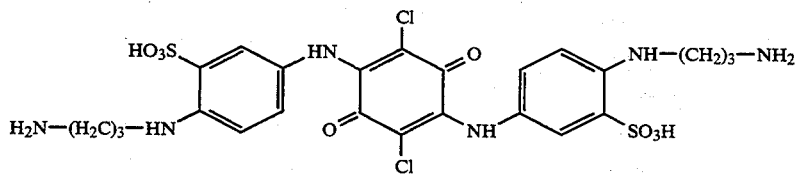

and 1 part of the compound of formula

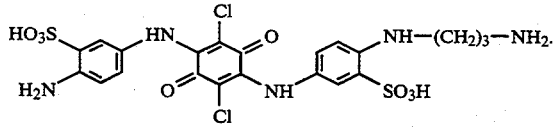

(A compound of the probable formula

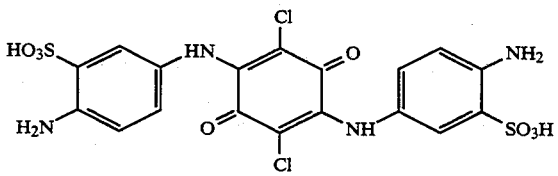

is present in the filtrate).

b) With stirring, 55 parts of the anil mixture obtained in a) are added in small portions at 0°-5° C. over 3 hours to 200 parts of 25% oleum. Then another 100 parts of 25% oleum are added dropwise, and the reaction mixture is stirred for 30 minutes at room temperature. Thereafter 52.3 parts of potassium peroxodisulfate are added in small portions over about 80 minutes such that the temperature does not rise above 30° C. The reaction mixture is then allowed to continue to react for about 30 minutes and subsequently poured into a mixture of ice/-water and stirred for about 15 minutes. The solid is isolated by filtration. The filter product is washed copiously with water and with ethanol and dried, giving the dioxazines of formulae in the ratio of about 1.2-1.4:1.

c) 76.8 parts of the mixture of dioxazine compounds obtained in b) are suspended in 750 parts of water and completely dissolved by adding sodium hydroxide solution. Over about 30 minutes, 7.5 parts of terephthaloyl dichloride in 60 parts of tetrahydrofuran (THF) are added dropwise to this solution, which has a pH of about 11.5, while keeping the pH at 11.5 by addition of sodium hydroxide solution. The reaction mixture is then kept for about 2 hours at room temperature and pH 11.5, while adding further sodium hydroxide solution. The pH is then adjusted to neutral with acetic acid and the reaction mixture is stirred for about 30 minutes after addition of sodium chloride and ethanol. The product is salted out, isolated by filtration and dried. It contains as main components a compound of each of formulae (1) and (16) as well as oligomers of formula (15), wherein A is 1,3-propylene, B is a radical of formula

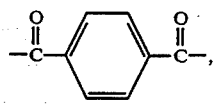

R and $R_1$ are each hydrogen, $R_2$ and $R_3$ are each chloro, X and $X_1$ are each —NH—, Z and $Z_1$ are each hydroxy, p and q are each 1, m and n are each 0, and t is 1, 2 or 3, and it dyes cotton in a brilliant blue shade of good allround fastness properties.

EXAMPLE 3 a) With good stirring, 80 parts of the compound of formula

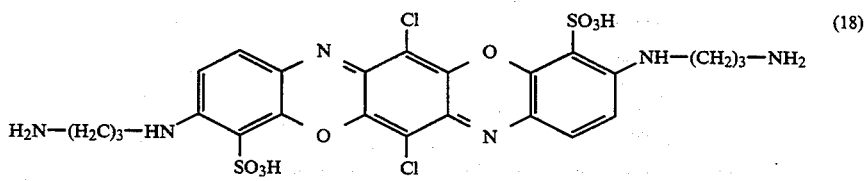

(18)

and

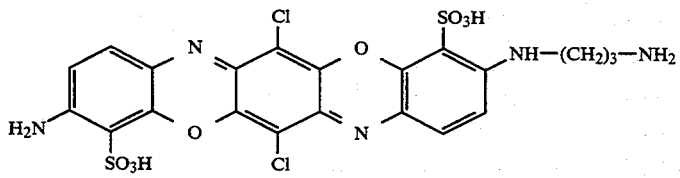

(17)

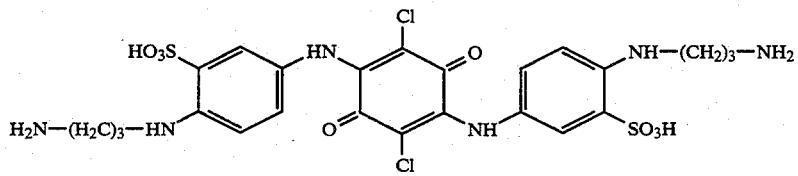

are added at room temperature over 40 minutes to 820 parts of oleum (25%). In the course of this addition, the temperature rises from initially 20°–25° C. to 40°–43° C., whereupon an olive-brown solution forms. After heating to 65° C. over 15 minutes, the reaction mixture is kept for 45 minutes at this temperature, whereupon the mixture gradually turns deep blue. After cooling to 20° C. on an ice-bath, the entire batch is cautiously poured (with external cooling) onto 4000 parts of ice, the temperature remaining below 30° C. Finally, 2500 parts of an aqueous solution of sodium hydroxide (30%) are added dropwise over about 1 hour, while keeping the temperature at 35° C. by cooling. Then, with good stirring, the batch is cooled to 20° C. and the precipitated product is filtered with suction. The filter product is washed with 2×1000 parts of water and dried with suction, giving 172 parts of a still moist crude product which, in the form of the free acid, corresponds to the mixture consisting of 70% by weight of the compound of formula

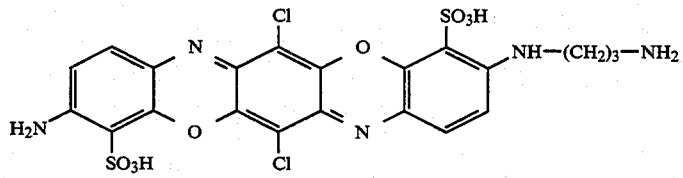

(17)

and 30% by weight of the compound of formula

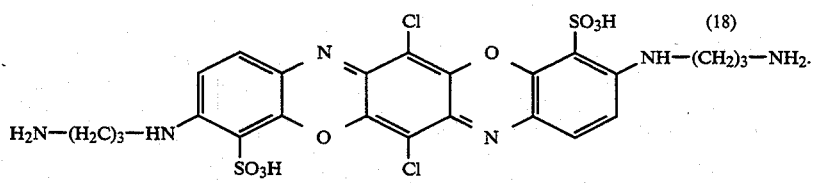

(18)

b) 25.6 parts of the above mixture consisting of 70% by weight of the compound of formula (17) and 30% by weight of the compound of formula (18) are suspended in 250 parts of water and completely dissolved by adding sodium hydroxide solution. Over about 30 minutes, 2.5 parts of terephthaloyl dichloride in 20 parts of tetrahydrofuran (THF) are added dropwise to this solution, which has a pH of about 11.5, while keeping the pH at 11.5 by addition of sodium hydroxide solution. The reaction mixture is then kept for about 2 hours at room temperature and pH 11.5, while adding further sodium hydroxide solution. The pH is then adjusted to neutral with acetic acid and the reaction mixture is stirred for about 30 minutes after addition of sodium chloride and ethanol. The product is salted out, isolated by filtration and dried. It contains as main components a compound of each of formulae (1) and (16) as well as oligomers of formula (15), wherein A is 1,3-propylene, B is a radical of formula

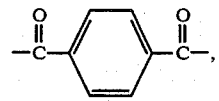

R and $R_1$ are each hydrogen, $R_2$ and $R_3$ are each chloro, X and $X_1$ are each —NH—, Z and $Z_1$ are each hydroxy, p and q are each 1, m and n are each 0, and t is 1, 2 or 3, and it dyes cotton in a brilliant blue shade of good allround fastness properties.

EXAMPLES 4 TO 13

The procedure of Example 2 is repeated, but replacing 38.1 parts of 4-(3-aminopropylamino)aniline-3-sulfonic acid in step a) of Example 2 with an equimolar amount of one of the anilino compounds listed in column 2 of Table 1, to give comparable mixtures of dyes which dye cotton in a brilliant blue shade of good allround fastness properties.

TABLE 1

| Ex. | Anilino compound |
|---|---|
| 4 | H$_2$N—⌬—NH—CH$_2$—CH(OH)—CH$_2$—NH$_2$ (with SO$_3$H on ring) |
| 5 | H$_2$N—⌬—NH—(CH$_2$)$_2$—NH$_2$ (with SO$_3$H on ring) |

TABLE 1-continued

| Ex. | Anilino compound |
|---|---|
| 6 | H$_2$N—⟨benzene with SO$_3$H⟩—NH—(CH$_2$)$_4$—NH$_2$ |
| 7 | H$_2$N—⟨benzene with SO$_3$H⟩—NH—⟨cyclohexyl⟩—NH$_2$ |
| 8 | H$_2$N—⟨benzene with SO$_3$H⟩—NH—CH$_2$—CH(CH$_3$)—NH$_2$ |
| 9 | H$_2$N—⟨benzene with SO$_3$H⟩—NH—(CH$_2$)$_2$—O—(CH$_2$)$_2$—NH$_2$ |
| 10 | H$_2$N—⟨benzene with SO$_3$H⟩—NH—(CH$_2$)$_2$—NH—(CH$_2$)$_2$—OH |
| 11 | H$_2$N—⟨benzene with SO$_3$H⟩—NH—⟨benzene with SO$_3$H⟩—NH$_2$ |
| 12 | H$_2$N—⟨benzene with SO$_3$H⟩—NH—⟨benzene with HO$_3$S and SO$_3$H⟩—NH$_2$ |
| 13 | H$_2$N—⟨benzene with SO$_3$H⟩—NH—⟨benzene with SO$_3$H⟩—(CH$_2$)$_2$—NH$_2$ |

TABLE 2

| Ex. | Dicarbonyl and disulfonyl chlorides |
|---|---|
| 14 | ClOC—⟨C$_6$H$_4$⟩—⟨C$_6$H$_4$⟩—COCl |
| 15 | ClOC—⟨C$_6$H$_4$⟩—CH=CH—⟨C$_6$H$_4$⟩—COCl |
| 16 | ClOC—⟨thiophene-2,5-diyl⟩—COCl |
| 17 | ClOC—COCl (oxalyl chloride) |
| 18 | ClOC—CH$_2$—⟨C$_6$H$_4$ (1,4)⟩—CH$_2$—COCl |
| 19 | ClOC—CH$_2$—⟨C$_6$H$_4$ (1,3)⟩—CH$_2$—COCl |
| 20 | ClOC—⟨C$_6$H$_4$⟩—CH$_2$—COCl |
| 21 | ClOC—CH=CH—COCl |
| 22 | ClOC—(CH$_2$)$_4$—COCl |
| 23 | ClSO$_2$—⟨C$_6$H$_4$ (1,3)⟩—SO$_2$Cl |
| 24 | naphthalene-1,5-disulfonyl chloride |
| 25 | naphthalene-2,6-disulfonyl chloride |

EXAMPLES 14 TO 25

The procedure of Example 2 is repeated, but replacing 7.5 parts of terephthaloyl dichloride in step c) of Example 2 with an equimolar amount of one of the dicarbonyl or disulfonyl chlorides listed in column 2 of Table 2, to give comparable mixtures of dyes which dye cotton in a brilliant blue shade of good allround fastness properties.

EXAMPLE 26

12.65 parts of the mixture of compounds of formulae (17) and (18) obtainable according to step a) of Example 3 (49.2% purity)) are suspended in 140 parts of water and dissolved by stirring for 2.5 hours at room temperature with 1.57 parts of lithium hydroxide x H$_2$O. Then 1.26 parts of toluylene-2,4-diisocyanate, dissolved in 5 parts of dioxane, are added dropwise at a temperature of 10° C. over 1 hour. When the condensation is complete, the reaction mixture is acidified with hydrochloric acid and the precipitated product is filtered with suction, giving 7 parts of a blue powder. This product contains as main component a compound of each of formulae (1) and (16) as well as oligomers of formula (15), wherein A is 1,3-propylene, B is a radical of formula

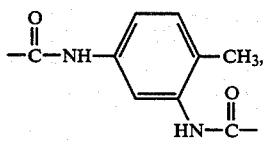

R and $R_1$ eare each hydrogen, $R_2$ and $R_3$ are each chloro, X and $X_1$ are each —NH—, Z and $Z_1$ are each hydroxy, p and q are each 1, m and n are each 0, and t is 1, 2 or 3, and it dyes cotton in a brilliant blue shade of good allround fastness properties.

EXAMPLES 27 TO 32

The procedure of Example 26 is repeated, but replacing 1.26 parts of toluylene-2,4-diisocyanate with an equimolar amount of one of the isocyano or isothiocyano compounds listed in column 2 of Table 3, to give comparable mixtures of dyes which dye cotton in a brilliant blue shade of good allround fastness properties.

TABLE 3

| Ex. | Isocyano and isothiocyano compounds |
|---|---|
| 27 | 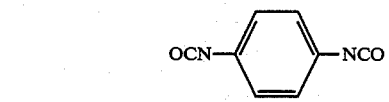 |
| 28 | 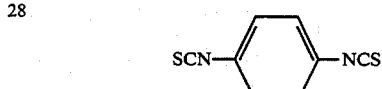 |
| 29 | 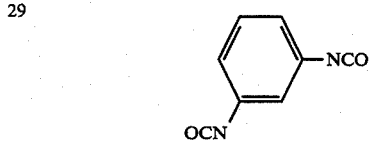 |
| 30 | OCN—⬡—NCO |
| 31 | (structure with H3C, CH2NCO, CH3, OCN, CH3) |
| 32 | OCN—(CH₂)₆—NCO |

EXAMPLE 33

34.3 parts of 4,4'-diaminostilbene-2,2'-disulfonic acid in 600 parts of water are condensed with 27.7 parts of cyanuric chloride at pH 1–2. The solution of the reaction product is added dropwise over about 15 minutes at room temperature to a solution containing 191.5 parts of a mixture consisting of 70% by weight of the compound of formula (17) as indicated above and 30% by weight of the compound of formula (18) as indicated above and 1000 parts of water. During this condensation reaction, the pH is kept constant at about 9.5 by addition of sodium hydroxide solution. After further reaction for 8 to 15 hours, 26.2 parts of morpholine are added to the reaction mixture, which is thereafter heated for about 3 hours under reflux (about 90°–95° C.). After cooling, the pH is adjusted to 6.5–7 and the product is salted out with sodium chloride. The isolated and dried product contains as main component a compound of each of formulae (1) and (16) as well as oligomers of formula (15), wherein A is 1,3-propylene, B is a radical of formula

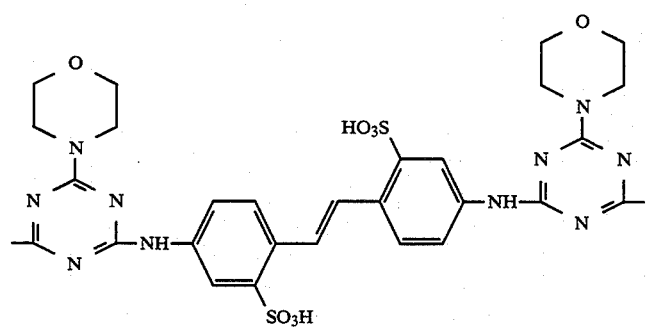

R and $R_1$ are each hydrogen, $R_2$ and $R_3$ are each chloro, X and $X_1$ are each —NH—, Z and $Z_1$ are each hydroxy, p and q are each 1, m and n are each 0, and t is 1, 2 or 3, and it dyes cotton in a greenish blue shade of good allround fastness properties.

Dyeing instruction I 12.5 parts of a non-mercerised, unbleached cotton fabric are wetted with one part of a nonionic wetting agent at a temperature of 80° C. The cotton is put into a dye solution which contains 2% of the dye mixture obtained in step b) of Example 3 and 2 g/l of sodium sulfate. The liquor ratio is 1:20. The dyebath is then heated to a temperature of 95° C. over 30 minutes, 8 g/l of sodium sulfate are added and the dyebath is left for 45 minutes at 95° C., cooled to 80° C., and left for 15 minutes at this temperature. The goods are then rinsed with water and dried, to give a cotton fabric which is dyed in a clear blue shade of good allround fastness properties.

Dyeing instruction II 12.5 parts of polyamide 66 fabric are put at 40° C. into a dyebath which has been adjusted to pH 6 by addition of 2 g/l of a phosphate buffer. The liquor ratio is 1:20. After 10 minutes 2% of the dye mixture obtained in step b) of Example 3 are added and the dyebath is heated to the boil over 45 minutes and left for 45 minutes at this temperature. The goods are rinsed with water and dried, to give a polyamide 66 fabric which is dyed in a clear blue shade of good allround fastness properties.

What is claimed is:

1. A dye mixture obtainable by condensing a compound of the formula

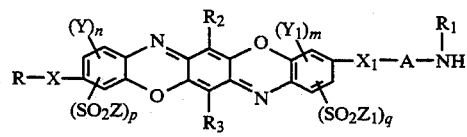 (8)

and a compound of the formula

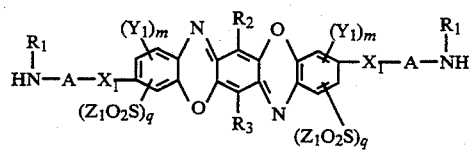 (10)

with a compound of formula

T—B—T (9)

wherein

R and $R_1$ are each independently of the other hydrogen; unsubstituted $C_1$–$C_4$alkyl or $C_1$–$C_4$alkyl which is substituted by hydroxy, sulfo, sulfato, chloro, cyano or acetoxy and, with the exception of methyl, may be interrupted by a group —O—; cyclopentyl or cyclohexyl which are unsubstituted or substituted by 1 to 3 methyl groups; unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl; unsubstituted 1- or 2-naphthyl or 1- or 2-naphthyl which is substituted by sulfo, nitro or chloro; or unsubstituted benzyl or benzyl which is substituted by methyl, methoxy, sulfo or chloro, X is a direct bond, —O—, —S— or —N($R_4$)—, wherein $R_4$ has the meanings given above for R and $R_1$, $X_1$ is —O—, —S— or —N($R_4$)—, wherein $R_4$ has the meanings given above for R and $R_1$, Y and $Y_1$ are each independently of the other $C_1$–$C_4$alkyl, $C_1$–$C_4$alkoxy, halogen, sulfo, carboxy, carbamoyl, N-mono- or N,N-di-$C_1$–$C_4$alkylcarbamoyl, N-phenyl- or N,N-diphenylcarbamoyl, sulfamoyl, N-mono- or N,N-di-$C_1$–$C_4$alkylsulfamoyl or N-phenyl- or N,N-diphenylsulfamoyl, Z and $Z_1$ are each independently of the other hydroxy or $C_1$–$C_4$alkyl, $R_2$ and $R_3$ are each independently of the other hydrogen, halogen, cyano, $C_1$–$C_4$alkyl, $C_1$–$C_4$alkoxy, sulfo, carboxy, carbamoyl, phenylcarbamoyl or $C_2$–$C_5$alkanoylamino; or phenyl, benzyl, benzoylamino or phenoxy each of which is unsubstituted or substituted in the phenyl ring by $C_1$–$C_4$alkyl, $C_1$–$C_4$alkoxy, acetylamino, halogen, nitro or sulfo, A is a linear or branched $C_2$–$C_6$alkylene radical which is unsubstituted or substituted by hydroxy, sulfo, sulfato, $C_1$–$C_4$alkoxy, carboxy, cyano, halogen, phenyl, sulfophenyl or $C_2$–$C_5$alkoxycarbonyl, and which may be interrupted by 1 or 2 —O— or —N($R_5$)— groups, wherein $R_5$ is $C_1$–$C_4$alkyl, acetyl or hydrogen, or by —S— or —SO$_2$—; or is a cyclohexylene radical which is unsubstituted or substituted by 1 to 3 methyl groups; or is a phenylene, biphenylene or naphthylene radical which is unsubstituted or substituted by $C_1$–$C_4$alkyl, $C_1$–$C_4$alkoxy, sulfo, halogen or carboxy; or is a $C_1$–$C_6$alkylene-phenylene, phenylene-$C_1$–$C_6$alkylene-phenylene, $C_1$–$C_3$alkylene-phenylene-$C_1$–$C_3$alkylene or methylene-naphthylene-methylene radical, wherein the phenylene and naphthylene moieties contain no further substituents or additionally carry 1 or 2 substituents selected from the group consisting of sulfo, carboxy, sulfamoyl, carbamoyl, methyl, ethyl, methoxy, ethoxy, nitro, chloro, amino, N-methylamino and N-ethylamino, N,N-dimethylamino and N,N-diethylamino and phenylamino, m, n, p and q are each independently of one another 0 or 1, T is halogen and B has the formula

  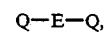 (2)

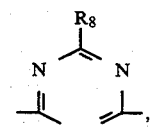 (3)

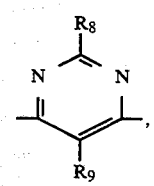 (4)

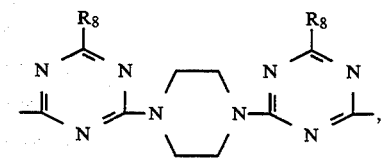 (5)

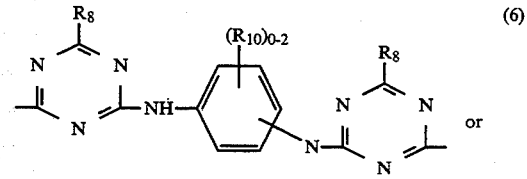 (6)

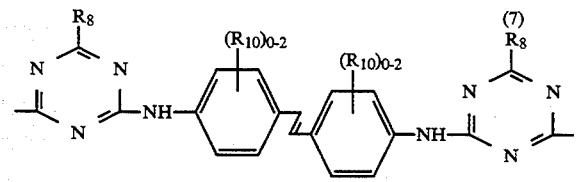 (7)

wherein Q is a group $$-\overset{O}{\underset{\|}{C}}-,\ -\overset{O}{\underset{\|}{C}}-NH-,\ -\overset{O}{\underset{\underset{\|}{O}}{\overset{\|}{S}}}-\ \text{or}\ -\overset{S}{\underset{\|}{C}}-NH-,$$

E is a direct bond; linear or branched $C_1$–$C_6$alkylene or $C_2$–$C_6$alkenylene which are unsubstituted or substituted by hydroxy, sulfo, sulfato, methoxy, carboxy, phenyl or sulfophenyl; or is cyclohexylene or $C_1$–$C_2$alkylene-cyclohexylene which are unsubstituted or substituted by 1 to 3 methyl groups; or is piperazine-1,4-diyl; thiophene-2,5-diyl; biphenyl-4,4'-diyl; stilbene-4,4'-diyl; unsubstituted phenylene or naphthylene or phenylene or naphthylene which are substituted by $C_1$–$C_4$alkyl, $C_1$–$C_4$alkoxy, sulfo, halogen or carboxy; or is $C_1$–$C_3$alkylene-phenylene or $C_1$–$C_2$alkylenephenylene-$C_1$–$C_2$alkylene which are unsubstituted or substituted in the phenyl moiety by methyl, methoxy, chloro or sulfo, $R_9$ is nitro, cyano, $C_1$–$C_4$alkylsulfonyl, carboxy, chloro, fluoro, $C_1$–$C_4$alkoxysulfonyl, $C_1$–$C_4$alkylsulfinyl, $C_1$–$C_4$alkoxycarbonyl or $C_1$–$C_4$alkanoyl, $R_{10}$ is sulfo, $C_1$–$C_4$alkyl, $C_1$–$C_4$alkoxy or halogen, and $R_8$ is chloro; hydroxy; $C_1$–$C_4$alkyl; phenyl; $C_1$–$C_4$alkoxy; $C_1$–$C_4$alkylthio; amino; N-mono- or N,N-di-$C_1$–$C_4$alkylamino which is unsubstituted or substituted in the alkyl moiety by hydroxy, carboxy, cyano, sulfo, sulfato or $C_1$–$C_4$alkoxy; cyclohexylamino; phenylamino or N-$C_1$–$C_4$alkyl-N-phenylamino which are unsubstituted or substituted in the phenyl moiety by $C_1$–$C_4$alkyl, $C_1$–$C_4$alkoxy, phenoxy, carboxy, sulfo or halogen; morpholino or 3-carboxy- or 3-carbamoylpyridin-1-yl.

2. A dye mixture according to claim 1, wherein R and $R_1$ are each independently of the other hydrogen, $C_1$–$C_4$alkyl, cyclohexyl, unsubstituted phenyl or benzyl, or phenyl or benzyl which are substituted by sulfo, chloro, methyl or methoxy.

3. A dye mixture according to claim 1, wherein R and $R_1$ are each hydrogen.

4. A dye mixture according to claim 1, wherein A is a $C_2$–$C_4$alkylene radical which is unsubstituted or substituted by hydroxy, sulfo, sulfato, methoxy, carboxy, or sulfophenyl, —$CH_2$—$CH_2$—$Z'$—$CH_2$—$CH_2$—, wherein $Z'$ is —O—, —S—, —$SO_2$—, —NH— or —N($CH_3$)—, a cyclohexylene radical which is unsubstituted or substituted by 1 to 3 methyl groups, an unsubstituted or sulfo-substituted 1,3- or 1,4-phenylene radical, or a $C_1$–$C_3$alkylenephenylene or $C_1$–$C_2$alkylenephenylene-$C_1$–$C_2$alkylene radical, wherein the phenylene moiety is unsubstituted or substituted by methyl, methoxy, chloro or sulfo.

5. A dye mixture according to claim 1, wherein A is a $C_2$–$C_4$alkylene radical which is unsubstituted or substituted by hydroxy, sulfo, sulfato, methoxy, carboxy, or sulfophenyl.

6. A dye mixture according to claim 1, wherein A is 1,2-ethylene or 1,2- or 1,3-propylene which is unsubstituted or substituted by hydroxy or sulfato.

7. A dye mixture according to claim 1, wherein X is the group —N($R_4$)—, wherein $R_4$ is hydrogen, $C_1$–$C_4$alkyl, cyclohexyl, unsubstituted phenyl or benzyl, or phenyl or benzyl which are substituted by sulfo, chloro, methyl or methoxy.

8. A dye mixture according to claim 8, wherein $R_4$ is hydrogen or $C_1$–$C_4$alkyl.

9. A dye mixture according to claim 1, wherein m and n are each 0.

10. A dye mixture according to claim 1, wherein p and q are each 1 and Z and $Z_1$ are each hydroxy or $C_1$–$C_4$alkyl.

11. A dye mixture according to claim 1, wherein $R_2$ and $R_3$ are each hydrogen, fluoro, chloro, bromo, methyl, methoxy, acetylamino, phenoxy or cyano.

12. A dye mixture according to claim 1, wherein $R_2$ and $R_3$ are each chloro.

13. A dye mixture according to claim 1, wherein the organic linking group B has the formula $$Q'-E'-Q' \qquad (2'),$$

(3')

[triazine ring structure with $R_8'$]

(5')

[bis-triazine piperazine structure with $R_8'$]

(6')

[bis-triazine phenylene structure with $R_8'$ and $(R_{10}')_{0-1}$]

or

-continued

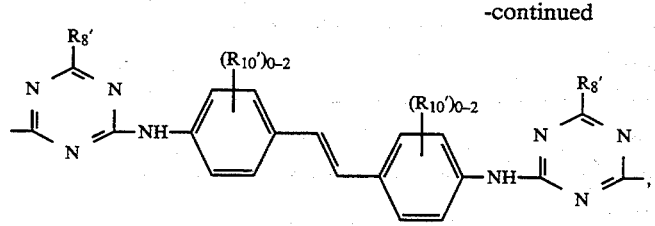 (7')

wherein Q' is a group

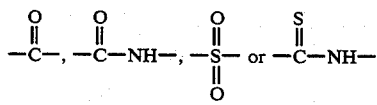

E' is a direct bond, $C_1$-$C_6$alkylene or $C_2$-$C_6$alkenylene which are unsubstituted or substituted by hydroxy, sulfo, sulfato, methoxy, carboxy, phenyl or sulfophenyl, or is cyclohexylene or $C_1$-$C_2$alkylene-cyclohexylene which are unsubstituted or substituted by 1 to 3 methyl groups, or is piperazine-1,4-diyl, thiophene-2,5-diyl, biphenyl-4,4'-diyl, stilbene-4,4'-diyl, unsubstituted phenylene or naphthylene, or phenylene or naphthylene which are substituted by $C_1$-$C_4$alkyl, $C_1$-$C_4$alkoxy, sulfo, halogen or carboxy, or is $C_1$-$C_3$alkylene-phenylene or $C_1$-$C_2$alkylene-phenylene-$C_1$-$C_2$alkylene which are unsubstituted or substituted in the phenyl moiety by methyl, methoxy, chloro or sulfo, R'$_8$ is chloro, hydroxy, $C_1$-$C_4$alkoxy, $C_1$-$C_2$alkylthio, amino, N-mono- or N,N-di-$C_1$-$C_4$alkylamino which are unsubstituted or substituted in the alkyl moiety by hydroxy, sulfo or sulfato, cyclohexylamino, phenylamino or N-$C_1$-$C_4$alkyl-N-phenylamino which are unsubstituted or substituted in the phenyl moiety by methyl, methoxy, carboxy, sulfo or chloro, or is morpholino, and R'$_{10}$ is sulfo, methyl or methoxy.

14. A dye mixture according to claim 1, wherein B is a linking group of formula

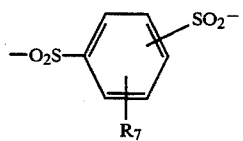

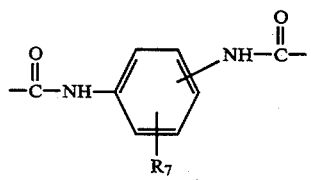

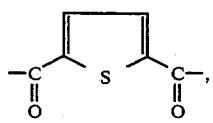

-continued

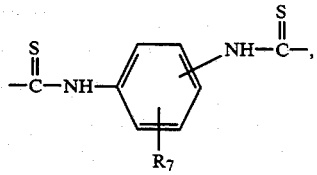

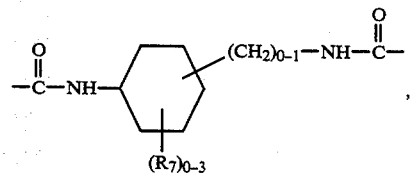

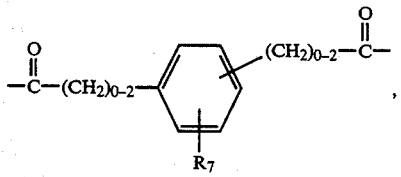

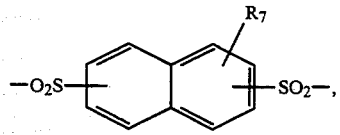

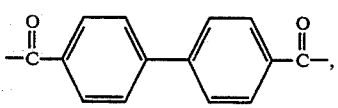

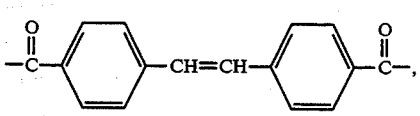

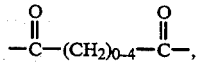

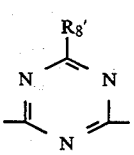

or

-continued

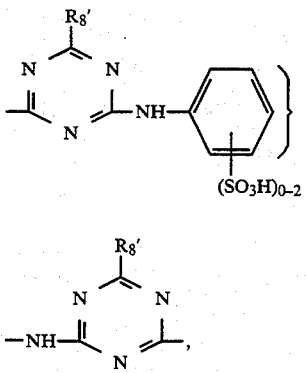

wherein R₇ is sulfo, methyl, methoxy, chloro, carboxy or hydrogen, and R'₈ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

15. A dye mixture according to claim 1, wherein B is a radical of formula

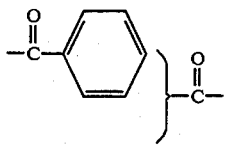

or

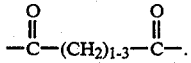

16. A dye mixture according to claim 1, wherein the compounds of formulae (8) and (10) are used in the weight ratio of 90:10 to 60:40.

17. A process for dyeing a polyester/cotton blend with a disperse dye and a direct dye, which comprises using a mixture of compounds obtainable according to claim 1 as the direct dye, in a one-step bath process and in addition to said disperse dye, and dyeing from an aqueous liquor in the temperature range from 100° to 150° C., and in the pH range from 4 to 7.5.

* * * * *